(12) United States Patent
Oikawa

(10) Patent No.: US 6,430,253 B1
(45) Date of Patent: Aug. 6, 2002

(54) CT APPARATUS

(75) Inventor: Shiro Oikawa, Shiga-ken (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 09/946,606

(22) Filed: Sep. 6, 2001

(30) Foreign Application Priority Data

Sep. 26, 2000 (JP) .................................. 2000-291666(P)

(51) Int. Cl.⁷ .............................................. G01N 23/00

(52) U.S. Cl. ............................................ 378/15; 378/4

(58) Field of Search ........................................ 378/4–20

(56) References Cited

U.S. PATENT DOCUMENTS 5,682,414 A * 10/1997 Saito ........................... 378/146
5,987,091 A * 11/1999 Miyazaki et al. ............. 378/15

OTHER PUBLICATIONS

"A solution to the long–object problem in helical cone–beam tomography," Phys. Med. Bio. 45 (2000), pp. 623–643.

* cited by examiner

Primary Examiner—Craig E. Church
(74) Attorney, Agent, or Firm—Rader, Fishman & Grauer PLLC

(57) ABSTRACT

In a CT apparatus, e.g. an X-ray CT apparatus, according to this invention, a plural scan executing unit executes a first and a second helical scans successively, with an X-ray tube and an X-ray detector each advancing along helical paths having a 180° phase difference (bisectional phase difference) therebetween. Consequently, CT image composing data is acquired from opposite directions for each point in an area of interest. That is, the CT image composing data obtained, as a whole, covers a scanning range corresponding to 360°. Then, an image reconstructing unit performs an image reconstructing process properly based on the CT image composing data collected through all the helical scans and covering the 360° scanning range. As a result, artifacts are restrained from appearing in CT images ultimately obtained.

16 Claims, 12 Drawing Sheets

CT APPARATUS

BACKGROUND OF THE INVENTION (1) Field of the Invention

This invention relates to a CT apparatus having an electromagnetic emitter for emitting electromagnetic waves in a conical form, and a planar detector, the emitter and detector being helically revolvable about an object under examination to scan the object. More particularly, the invention relates to a technique of suppressing artifacts appearing in CT images (computed tomographic images).

(2) Description of the Related Art

An X-ray CT apparatus may be cited as one example of CT apparatus that emits electromagnetic waves in a conical form and detects transmitted electromagnetic waves with a planar detector. Such an X-ray CT apparatus will be described below with reference to FIGS. 1 and 2.

As shown in FIG. 1, a conventional X-ray CT apparatus includes, opposed to each other across an object under examination M, an X-ray tube 51 for emitting an X-ray beam CB in a conical form, and a panel type X-ray detector 52 having a two-dimensional detecting surface 52a for detecting transmitted X rays. As shown in FIG. 2, the X-ray tube 51 and panel type X-ray detector 52 are movable about and relative to the object M. That is, a helical scanning is carried out by following a helical or spiral path SP and advancing along the body axis Z. As the X-ray tube 51 emits an X-ray beam CB in a conical form during a helical scanning operation of X-ray tube 51 and panel type X-ray detector 52, CT image composing data is collected from the X-ray detector 52. In this apparatus, the panel type X-ray detector 52 has numerous X-ray detecting elements arranged in a matrix form, and transmitted X-ray beams are detected in numerous detection lines succeeding one after another along the object's body axis. As a result, numerous slice images may be acquired from an area of interest Ma at a time, thereby reducing the time consumed in photography.

Further, an X-ray CT apparatus of this type has been proposed that collects from the panel type X-ray detector 52 CT image composing data covering a 180° scanning range for each point in the area of interest Ma (M. Defrise et al. "A solution to the long-object problem in helical cone-beam tomography" Phys. Med. Biol. 45 (2000) 623–643). The apparatus having the above construction is also called the PI-line detection area type. As shown in FIG. 3, when a cylindrical surface SQ including the helical path SP of X-ray tube 51 is regarded as a detection area, a projection data collection area is between helical curves (arcs uu' and dd') less than a pitch of helical path SP as seen from the X-ray tube 51. Since, in this case, the site-dependent weight function in time of reverse projection is simplified to speed up an image reconstructing process.

To supplement the above, when an X-ray beam CB in a conical form is used, the apparatus becomes the three-dimensional CT type which, unlike the usual two-dimensional CT type, complicates the relationship between each point in the area of interest and X-ray detection element, and complicates the site-dependent weight function in time of reverse projection. However, as shown in FIG. 3, when collecting from the panel type X-ray detector 52 CT image composing data covering a 180° scanning range from a scan position xs through a scan position xo to a scan position xe for each point P in an area of interest, there is an advantage that the relationship between each point in the area of interest Ma and X-ray detection element is relatively simple to simplify the site-dependent weight function in time of reverse projection. It will be appreciated that, for expediency of description, point P is shown as lying on the body axis Z in FIG. 3.

However, the conventional X-ray CT apparatus of the PI-line detection area type noted above has a disadvantage that artifacts tend to appear in a CT image ultimately obtained.

That is, with the PI-line detection area type, as shown in FIG. 4, artifacts could appear in the direction of a segment extending between scan positions xs and xe at opposite ends of the 180° scanning range for each point in the area of interest of object M. In principle, the same data should be obtained by emitting an X-ray beam CB in a conical form from opposite directions to point P in the area of interest. However, these data actually are not necessarily the same because of the non-parallelism of beam elements of X-ray beam CB and the polychroism of X rays. As a result, artifacts are created in reconstructing CT images.

SUMMARY OF THE INVENTION

This invention has been made having regard to the state of the art noted above, and its primary object is to provide an X-ray CT apparatus of the PI-line detection area type which is capable of suppressing artifacts appearing in CT images ultimately obtained.

The above object is fulfilled, according to this invention, by a CT apparatus for making a plurality of helical scans about an object under examination placed on a support table, and collecting, through each scan, CT image composing data covering a scanning range of 180° for each point in an area of interest, the CT apparatus comprising:

an electromagnetic wave emitting device for emitting electromagnetic waves in a conical form toward the object;

a planar detecting device opposed to the electromagnetic wave emitting device across the object for detecting the electromagnetic waves emitted from the electromagnetic wave emitting device and diverging two-dimensionally;

a drive device for moving the electromagnetic wave emitting device and the planar detecting device relative to the object while rotating the electromagnetic wave emitting device and the planar detecting device about the object, to cause electromagnetic waves to make helical scans around the object, whereby CT image composing data covering a 180° scanning range for each point in the area of interest of the object are collected from the planar detecting device;

a plural scan control device for controlling the drive device such that the plurality of helical scans made of the object by the electromagnetic wave emitting device have helical paths with a phase difference therebetween of 360° divided equally; and an image reconstructing device for performing an image reconstructing process based on CT image composing data collected through the plurality of helical scans.

In a tomographic process performed by the above CT apparatus, the plural scan control device executes a plurality of helical scans successively of an object under examination. At this time, as electromagnetic waves (e.g. X rays) are emitted in a conical form during each helical scan, CT image composing data covering a 180° scanning range is collected for each point in the area of interest. That is, this CT apparatus is the PI-line detection area type, in which the relationship between each point in the area of interest and each X-ray detection element of the planar detecting device is relatively simple to simplify a site-dependent weight function in time of reverse projection.

Further, since the helical scans are made to follow helical paths having an equi-sectional phase difference therebetween, CT image composing data is collected from a plurality of directions for each point in the area of interest through all the helical scans. That is, CT image composing data covering a 360° scanning range is acquired ultimately. The CT image composing data acquired is transmitted to the image reconstructing device to carry out an image reconstructing process based on the CT image composing data collected through all the helical scans and covering the 360° scanning range. By using the CT image composing data collected from a plurality of directions for each point in the area of interest, a discrepancy due to the non-parallelism of beam elements and the polychroism of beams is eliminated, whereby images are reconstructed properly. This suppresses artifacts appearing in X-ray CT images ultimately obtained.

In the CT apparatus according to this invention, the plural scan control device, preferably, is arranged to control the drive device to execute the helical scans to and fro by alternately reversing a scanning direction and a rotating direction for each scan. With this construction, the plural scan control device controls the drive device to execute the helical scans to and fro by alternately reversing the scanning direction and rotating direction for each scan. That is, after a helical scan from a starting end to a terminal end of the area of interest, a next helical scan is carried out from the terminal end back to the starting end, with the rotating direction also reversed. Since there is no need to perform a return scan between the two helical scans, images may be picked up in a short time.

In the CT apparatus according to this invention, the plural scan control device, preferably, is arranged to control the drive device to execute the helical scans to and fro and constantly in the same direction of rotation. With this construction, the plural scan control device controls a continuous photographic process with reciprocal helical scans in the same rotating direction, or a photographic process with helical scans in the same rotating direction and including a return scan in between. Thus, there is no need to switch the rotating direction for each helical scan.

In the CT apparatus according to this invention, the plural scan control device, preferably, is arranged to control the drive device to execute a non-helical, simple rotating scan in a range of π to 2π at each of opposite ends of each helical scan. With this construction, a non-helical, simple rotating scan takes place in a range of π to 2π at each of the opposite ends of each helical scan. Thus, sufficient CT image composing data is collected even at the opposite ends of each helical scan for which data tends to be insufficient.

In the CT apparatus according to this invention, the plural scan control device, preferably, is arranged to control the drive device to execute the helical scans having a phase difference therebetween of 360° divided equally by an even number or an odd number. With this construction, an image reconstructing process is carried out properly based on the CT image composing data acquired. This suppresses artifacts appearing in X-ray CT images ultimately obtained.

In the CT apparatus according to this invention, the plural scan control device, preferably, is arranged to control the drive device to execute the helical scans in a range of π multiplied by a multiple of 2. With this construction, image data may be picked up from an increased area of interest.

In the CT apparatus according to this invention, the plural scan control device, preferably, is arranged to control the drive device to execute a pre-scan before starting, and a post-scan after finishing, each helical scan effective to collect CT image composing data, the pre-scan and the post-scan being ineffective to collect CT image composing data. With this construction, the X-ray emitting device and planar detecting device may have a stable scanning speed when starting each scan for collecting CT image composing data. A post-scan carried out after each scan is effective to decelerate the X-ray emitting device and planar detecting device gradually, thereby to reduce the load applied to the apparatus.

In another aspect of this invention, a CT apparatus is provided for making a plurality of helical scans about an object under examination placed on a support table, and collecting, through each scan, CT image composing data covering a scanning range of 180° for each point in an area of interest, the CT apparatus comprising:

an electromagnetic wave emitting device for emitting electromagnetic waves in a conical form toward the object;

a planar detecting device opposed to the electromagnetic wave emitting device across the object for detecting the electromagnetic waves emitted from the electromagnetic wave emitting device and diverging two-dimensionally;

a drive device for moving the electromagnetic wave emitting device and the planar detecting device relative to the object while rotating the support table, to cause electromagnetic waves to make helical scans around the object, whereby CT image composing data covering a 180° scanning range for each point in the area of interest of the object are collected from the planar detecting device;

a plural scan control device for controlling the drive device such that the plurality of helical scans made of the object by the electromagnetic wave emitting device have helical paths with a phase difference therebetween of 360° divided equally; and an image reconstructing device for performing an image reconstructing process based on CT image composing data collected through the plurality of helical scans.

In a tomographic process performed by the above CT apparatus, the plural scan control device executes a plurality of helical scans successively, following helical paths having an equi-sectional phase difference therebetween. Thus, CT image composing data is collected from a plurality of directions for each point in the area of interest. CT image composing data covering a 360° scanning range is acquired. The image reconstructing device carries out an image reconstructing process properly based on the CT image composing data collected through all the helical scans and covering the 360° scanning range. This suppresses artifacts appearing in X-ray CT images ultimately obtained.

BRIEF DESCRIPTION OF THE DRAWINGS

For the purpose of illustrating the invention, there are shown in the drawings several forms which are presently preferred, it being understood, however, that the invention is not limited to the precise arrangement and instrumentalities shown.

DESCRIPTION OF THE PREFERRED EMBODIMENTS

Preferred embodiments of this invention will be described in detail hereinafter with reference to the drawings.

<First Embodiment>

One embodiment of this invention will be described with reference to the drawings.

Figure 5:
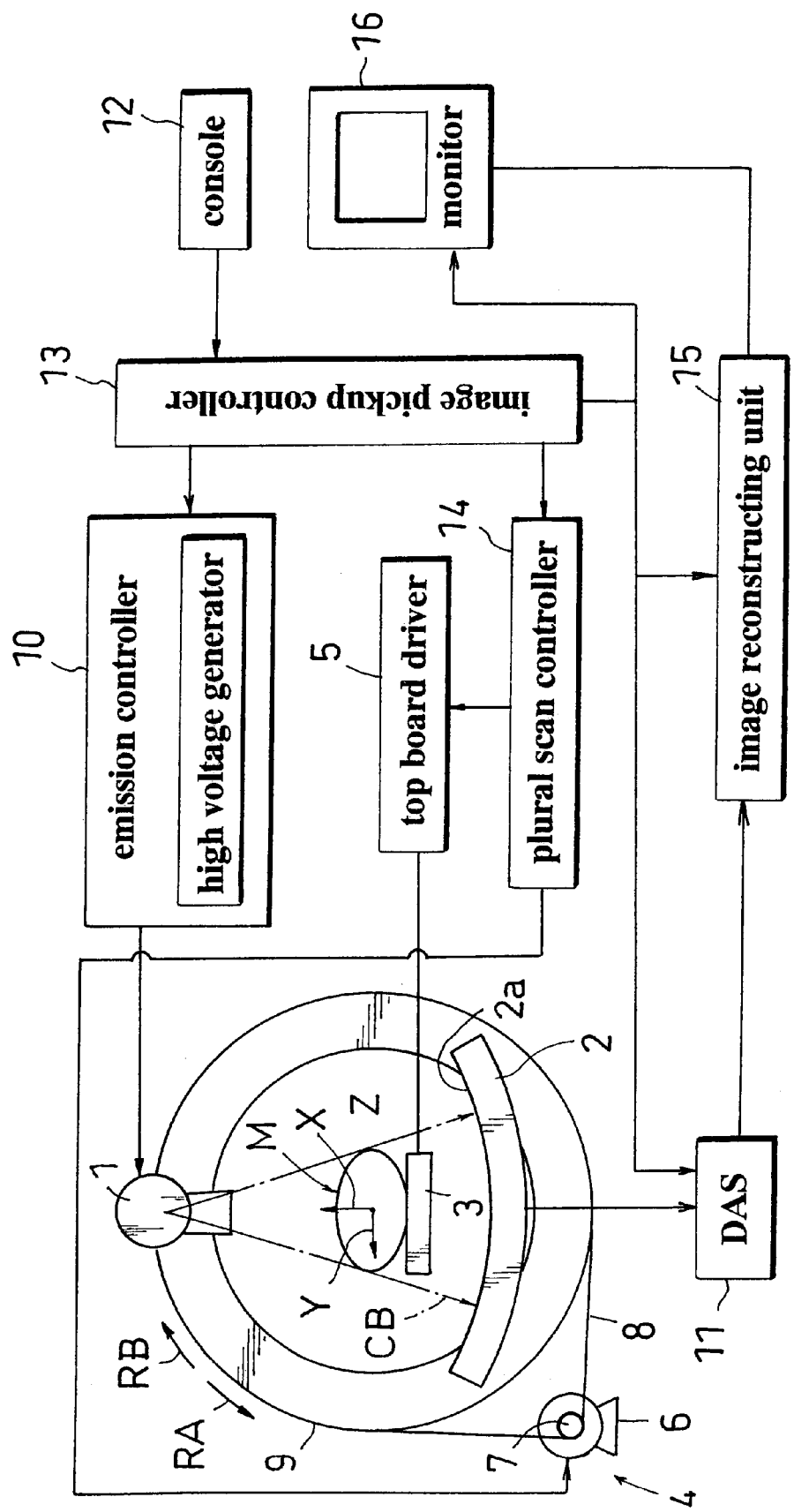
FIG. 5 is a block diagram of an entire X-ray CT apparatus in a first embodiment.

FIG. 5 is a block diagram showing an entire X-ray CT apparatus of the cone beam emitting type (which, where appropriate, will be referred to hereinafter simply as "X-ray CT apparatus") in a first embodiment.

Figure 6:
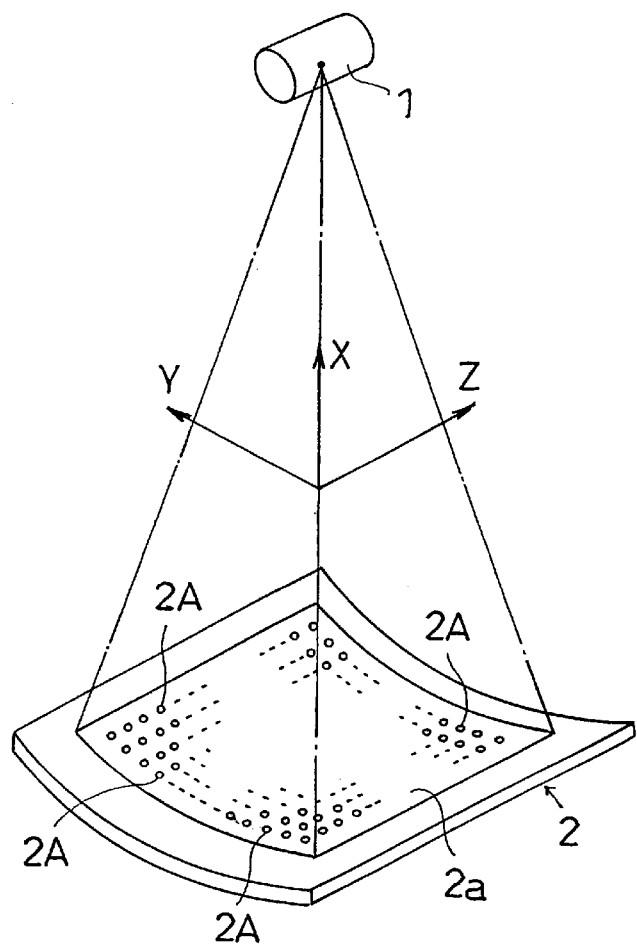
FIG. 6 is a perspective view showing an outline of an image pickup system of the X-ray CT apparatus in the first embodiment.
Figure 7:
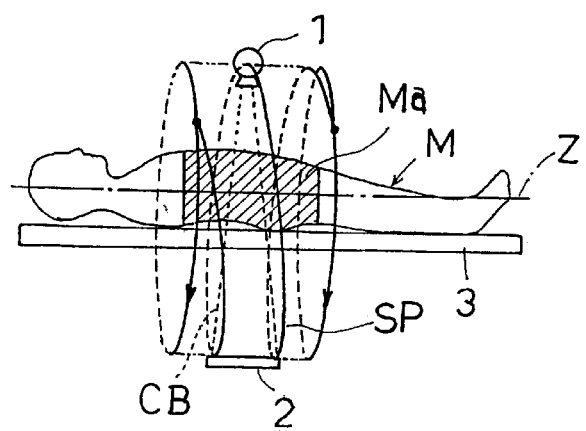
FIG. 7 is a front view showing a helical path in a helical scanning by the apparatus in the first embodiment.

The X-ray CT apparatus in the first embodiment of FIG. 5, as also shown in FIG. 6, includes an X-ray tube 1 for emitting an X-ray beam CB in a conical form toward a patient (object under examination) M on a top board (support table) 3, and a panel type X-ray detector 2 (which, where appropriate, will be referred to hereinafter simply as "X-ray detector") opposed to the X-ray tube 1 and having a two-dimensional detecting surface 2a for detecting transmitted X rays. As shown in FIG. 7, the X-ray tube 1 and X-ray detector 2 are movable about the patient M, and carry out a helical scanning by following a helical or spiral path SP and advancing along the body axis Z. While the X-ray tube 1 and X-ray detector 2 move together as opposed to each other across the patient M, the X-ray tube 1 emits a conical X-ray beam CB to the patient M, and CT image composing data is collected from the X-ray detector 2. An image reconstructing process is carried out based on the CT image composing data collected. The X-ray tube 1 in this embodiment corresponds to the electromagnetic emitting device of this invention. The panel type X-ray detector 2 corresponds to the planar detecting device.

Various components of the apparatus in the first embodiment will particularly be described hereinafter.

The X-ray CT apparatus in the first embodiment includes an image pickup system rotating mechanism 4 for rotating the X-ray tube 1 and X-ray detector 2 as opposed to each other across the patient M, and a top board driver 5 for reciprocating the top board 3, with the patient M placed thereon, along the body axis Z of patient M. A helical scanning is carried out by operating the rotating mechanism 4 to rotate the X-ray tube 1 and X-ray detector 2 about the body axis Z of patient M, and operating the top board driver 5 to move the top board 3 along the body axis Z of patient M.

The image pickup system rotating mechanism 4 has a rotating ring 9 rotatable by torque of a motor 6 transmitted through a pulley 7 and a belt 8. The X-ray tube 1 and X-ray detector 2 are fixedly arranged on the rotating ring 9. That is, as the rotating ring 9 rotates with a forward rotation or backward rotation of motor 6, the X-ray tube 1 and X-ray detector 2 opposed to each other rotate together in the direction indicated by an arrow RA or RB about the patient M.

The helical scanning may be carried out not by moving the top board 3 as well as the X-ray tube 1 and X-ray detector 2 as noted above, but by rotating the X-ray tube 1 and X-ray detector 2 and at the same time moving the X-ray tube 1 and X-ray detector 2 along the body axis Z of patient M, with the top board 3 fixed to maintain the patient M still.

The X-ray CT apparatus in the first embodiment further includes an emission controller 10 having a high voltage generator. Under control of this controller 10, the X-ray tube 1 emits a conical X-ray beam CB according to set irradiating conditions such as a tube voltage and a tube current.

The X-ray detector 2 has numerous X-ray detecting elements 2A arranged in a matrix form for detecting transmitted X-ray beams in numerous detection lines succeeding one after another along the body axis Z of patient M. As a result, numerous slice images may be acquired from an area of interest Ma at a time. In this embodiment, as shown in FIG. 6, the X-ray detector 2 is shaped to define a curved surface corresponding to part of a cylindrical surface. Instead, the X-ray detector may be shaped to define a completely flat surface.

The X-ray CT apparatus in this embodiment is the PI-line detection area type, in which, as a conical X-ray beam CB is emitted during a helical scanning, a data acquisition system (DAS) 11 collects from the X-ray detector 2 CT image composing data covering a 180° scanning range for each point in the area of interest Ma.

Figure 1:
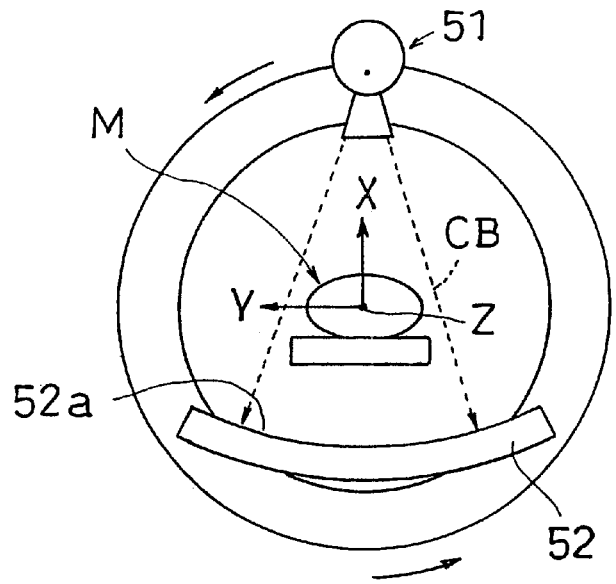
FIG. 1 is a schematic view showing a principal portion of an image pickup system in a conventional X-ray CT apparatus.
Figure 2:
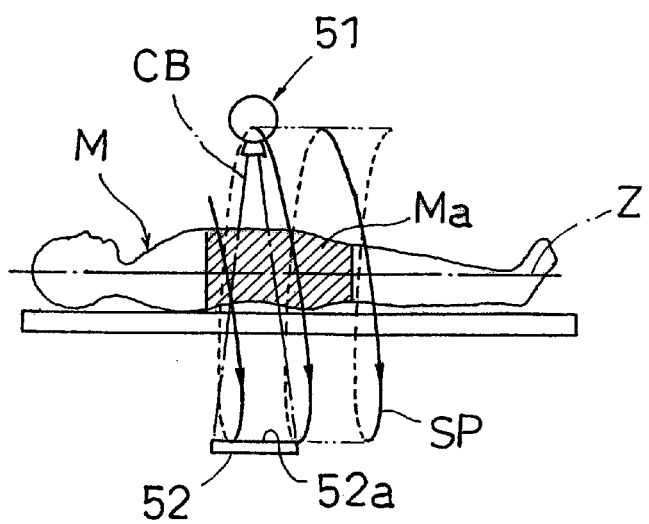
FIG. 2 is a front view showing a helical path in a helical scanning by the conventional X-ray CT apparatus.
Figure 3:
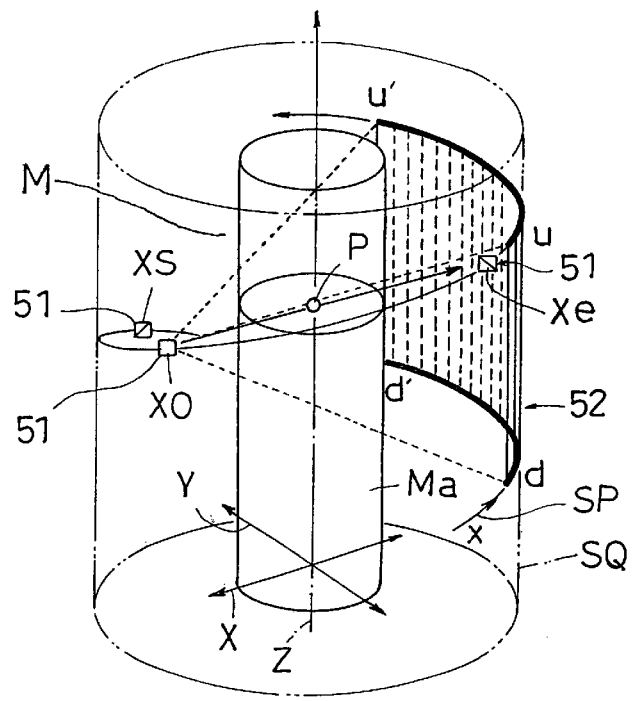
FIG. 3 is an explanatory view of an X-ray beam detection by the conventional X-ray CT apparatus.
Figure 4:
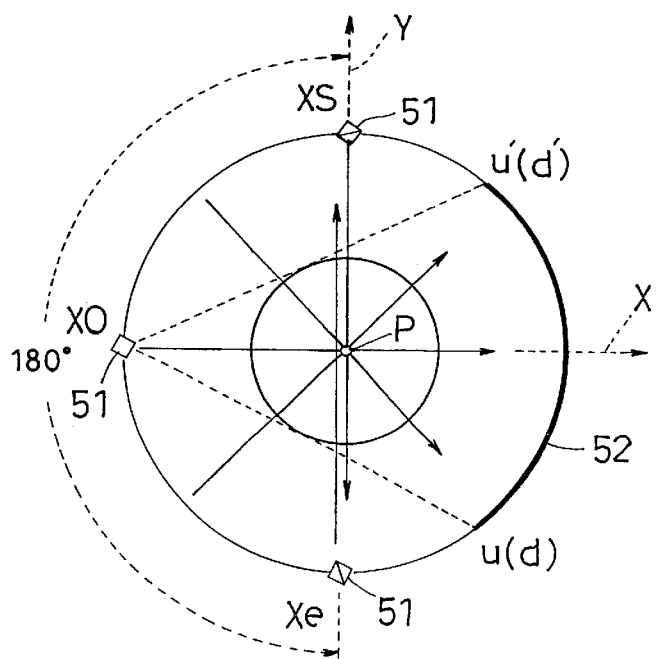
FIG. 4 is an explanatory view of an artifact generation by the conventional X-ray CT apparatus.

In the apparatus of the PI-line detection area type in the first embodiment, as shown in FIG. 3, when a cylindrical surface SQ including the helical path SP of the X-ray tube is regarded as a detection area, a projection data collection area is between helical curves (arcs uu' and dd') less than a pitch of helical path SP as seen from the X-ray tube. That is, the relationship between each point in the area of interest Ma and X-ray detection element is relatively simple to simplify a site-dependent weight function in time of reverse projection, thereby realizing a high-speed image reconstructing process.

The pickup system rotating mechanism 4, top board driver 5, emission controller 10 and data acquisition system (DAS) 11 are controlled by command signals outputted at appropriate times from an image pickup controller 13 based on set conditions inputted from a console 12 according to photographing conditions. The high voltage supply to the X-ray tube 1 and data fetching from the X-ray detector 2 in movement are effected through cables mounted in a gantry not shown.

The data fetching from the X-ray detector 2 is not limited to the use of the cable, but may be made by means of a slip ring or an optical isolator.

The X-ray CT apparatus in the first embodiment includes, as characteristic features thereof, a plural scan controller 14 for successively executing a plurality of helical scans with an equi-sectional phase difference between helical paths followed by the X-ray tube 1 and X-ray detector 2, and an image reconstructing unit 15 for performing an image reconstructing process based on CT image composing data collected through the plurality of helical scans. The plural scan controller 14 in this embodiment corresponds to the plural scan control device of this invention. The image reconstructing unit 15 corresponds to the image reconstructing device.

Operation of the above characteristic construction will particularly be described below.

Figure 8A:
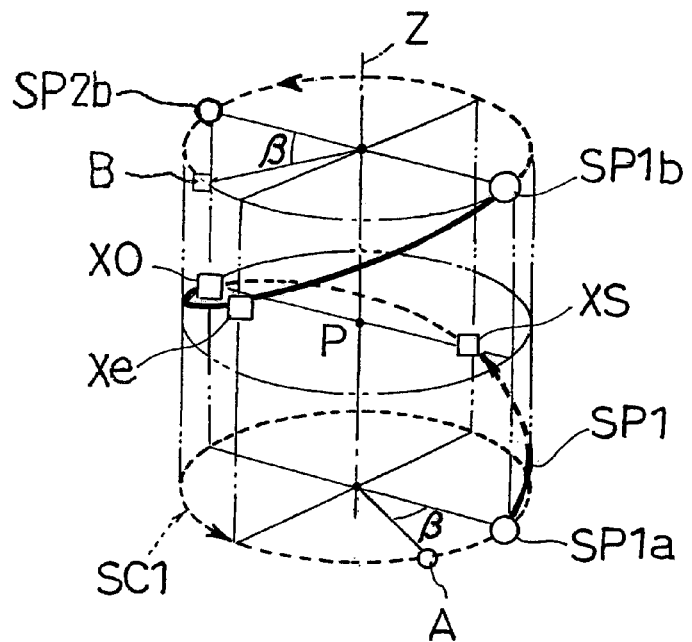
FIG. 8A is an explanatory view of a scan mode by the X-ray CT apparatus in the first embodiment, showing a path of a first helical scan.
Figure 8B:
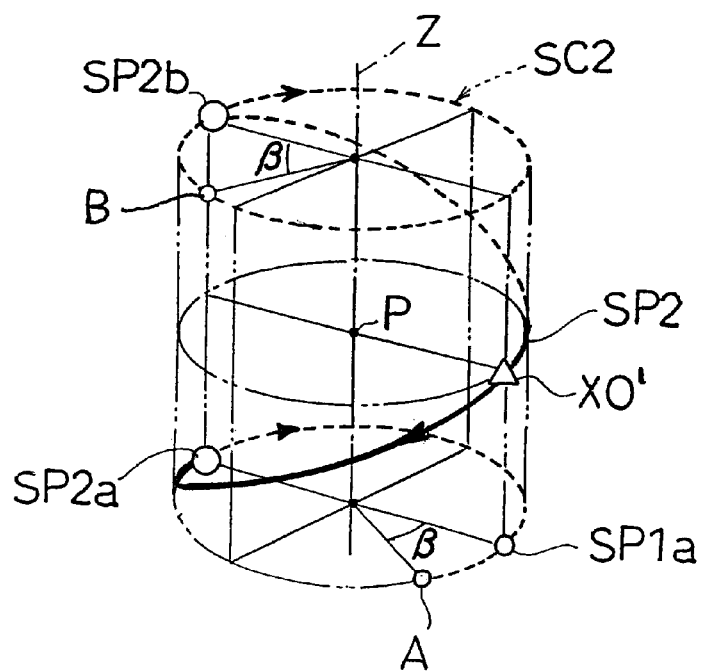
FIG. 8B is an explanatory view of a scan mode by the X-ray CT apparatus in the first embodiment, showing a path of a second helical scan.

The plurality of scans executed by the plural scan controller 14 include a first helical scan as shown in FIG. 8A in which the X-ray tube 1 moves along a helical path SP1, and a second helical scan as shown in FIG. 8B in which the X-ray tube 1 moves along a helical path SP2, the two scans being executed successively. At this time, the helical path SP1 and helical path SP2 have a phase difference of 180° (bisectional phase difference) therebetween. That is, the helical path SP1 and helical path SP2 are the same in shape, with a 180° shift between points SP1$a$ and SP2$a$ at the starting end of the area of interest Ma, and between points SP1$b$ and SP2$b$ at the terminal end of the area of interest Ma. The first helical scan and second helical scan cover a scanning range corresponding to 2pi. Naturally, the plural scan controller 14 controls the image pickup system rotating mechanism 4 and top board driver 5 to perform the first and second helical scans.

For expediency of illustration, only the helical paths of X-ray tube 1 are shown in FIGS. 8A and 8B noted above, and in FIGS. 14A through 14D, FIGS. 15A through 15C and FIG. 16 to be referred to hereinafter. It will be appreciated that the X-ray detector 2 is movable, together with and as opposed to the X-ray tube 1, in similar scanning/rotating directions. Further, the body axis Z of patient M is shown as extending upward.

As shown in FIGS. 8A and 8B, the plural scan controller 14 executes non-helical, simple rotating scans SC1 and SC2 of 2π (360°) at the starting end and terminal end of each helical scan. Before the simple rotating scans SC1 and SC2, respectively, a pre-scan without photography is carried out to ensure scanning stability, and a post-scan is carried out to reduce the load applied to the apparatus by a sudden stop of the scan after photography. Specifically, as shown in FIGS. 8A and 8B, the pre-scan is made through an angle β from a point A to the starting points SP1$a$ of the first helical scan, which is followed by the simple rotating scan SC1 and the first helical scan.

Upon arrival at the terminal end of the first helical scan, the X-ray tube 1 moves toward the starting point SP2$b$ of the second helical scan. At this time, the X-ray tube 1 moves as far as a point B which is beyond the starting point SP2$b$ of the second helical scan by the angle β allowing for a pre-scan required before starting the simple rotating scan SC2. That is, this angle β corresponds also to the post-scan. The angle β is determined appropriately based on photographing and other conditions.

Next, before starting the second helical scan, as shown in FIG. 8B, a pre-scan and simple rotating scan SC2 are performed in a scanning direction reversed from the simple rotating scan SC1 executed at the starting end. Then, the second helical scan is executed immediately thereafter. The X-ray tube 1 having returned to the starting end carries out the same operation as at the terminal end.

That is, in this embodiment, after finishing the first helical scan, a return scan is not carried out but a second helical scan is carried out continuously by reversing the scanning direction and rotating direction.

Figure 9:
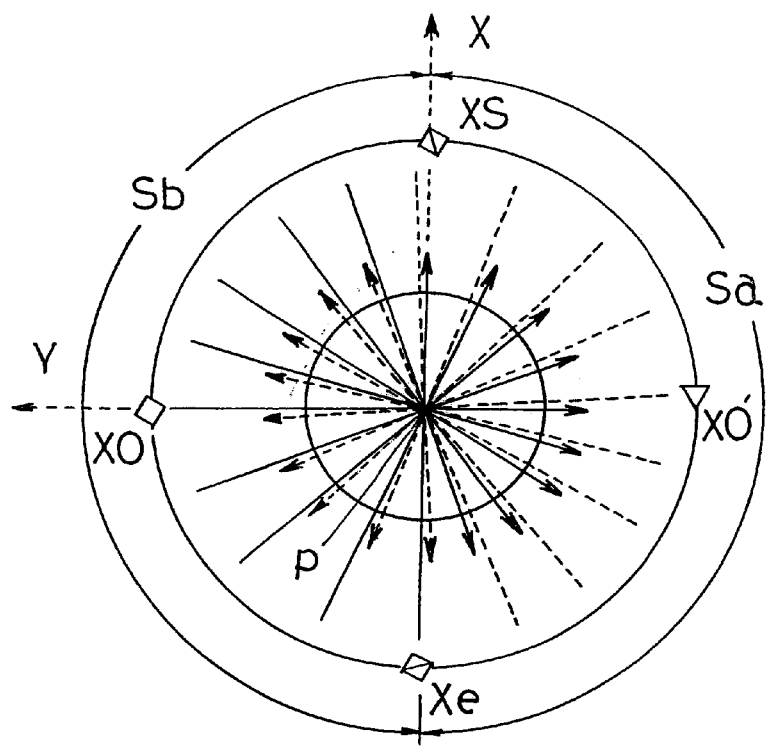
FIG. 9 is a schematic view of a collection of CT image composing data through the first and second helical scans by the apparatus in the first embodiment.
Figure 10:
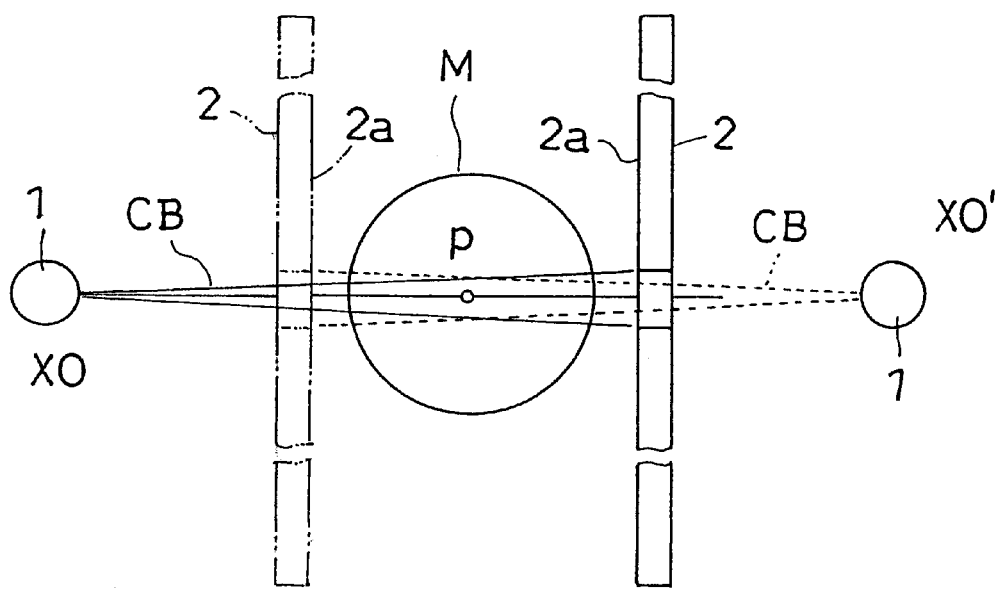
FIG. 10 is an explanatory view of photography made from two opposite directions by the apparatus in the first embodiment.

Thus, as shown in FIG. 9, the apparatus in the first embodiment collects, for each point P (shown, for expediency, to be lying on the body axis Z in FIGS. 8A and 8B) in the area of interest Ma, CT image composing data covering a 180° scanning range Sa by the first helical scan, and CT image composing data covering the remaining 180° scanning range Sb by the succeeding second helical scan. As a result, as shown in FIG. 10, CT image composing data is collected from opposite directions for each point in the area of interest, and CT image composing data covering a 360° scanning range is acquired ultimately. In addition, through the simple rotating scans SC1 and SC2 at the opposite ends of each helical scan, sufficient CT image composing data is collected even at the opposite ends of each helical scan for which data tends to be insufficient unless such simple rotating scans are performed.

Further, the image reconstructing unit 15 carries out an image reconstructing process based on the 360° CT image composing data collected through the first and second helical scans, and the CT image composing data collected through the simple rotating scans SC1 and SC2. In this image reconstructing process, a discrepancy due to the non-parallelism of beam elements and the polychroism of beams is eliminated with the CT image composing data collected from two opposite directions for each point in the area of interest Ma, whereby images are reconstructed properly. This suppresses artifacts appearing in final X-ray CT images.

Figure 11:
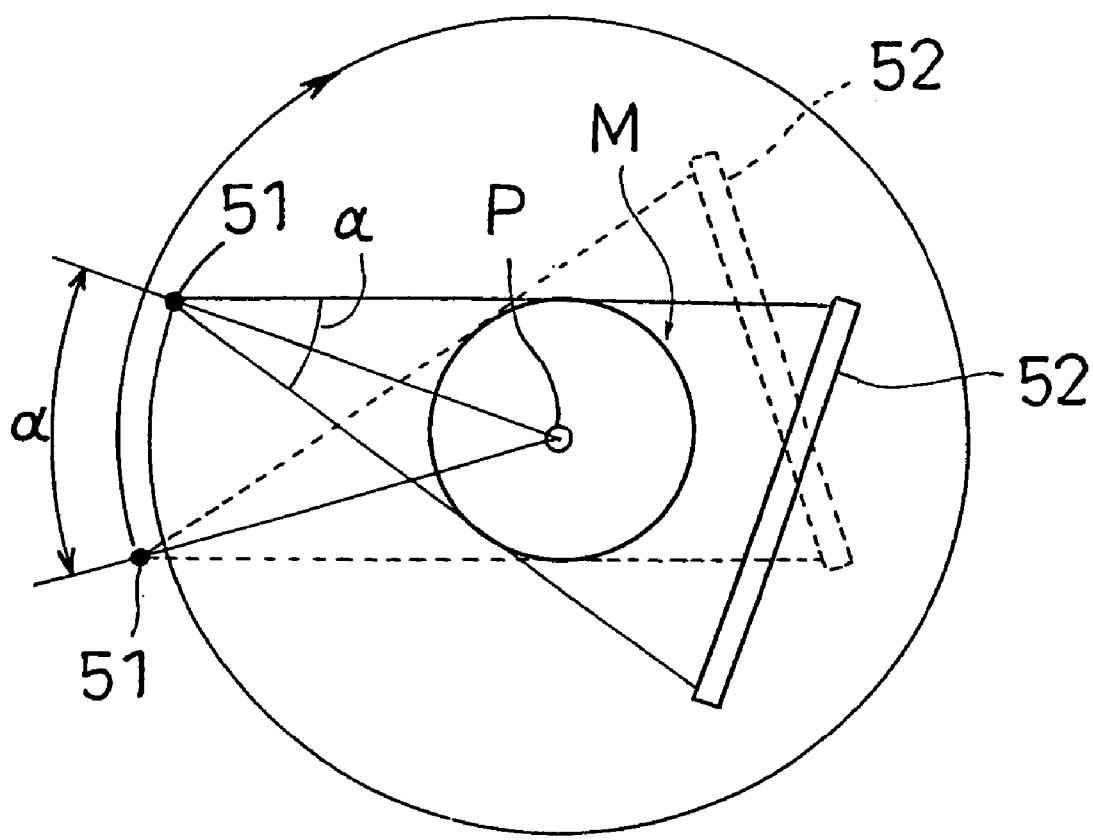
FIG. 11 is a schematic view showing an X-ray beam detection in a two-dimensional CT mode.

The plural scan controller 14 in this embodiment may be modified to execute a non-helical, simple rotating scan of π (180°), instead of the simple rotating scan (360°) SC1 or SC2, at each of the opposite ends of a helical scan, to collect extra CT image composing data at the opposite ends of each helical scan for which data tends to be insufficient. In this simple scan π (180°), as shown in FIG. 11, a conical X-ray beam is emitted with the center point thereof constantly passing through the point P. Actually, therefore, CT image composing data is collected from a region corresponding to an angle 180°+α which is an opening angle (+)α of the conical X-ray beam CB added to the simple scan π.

Figure 12:
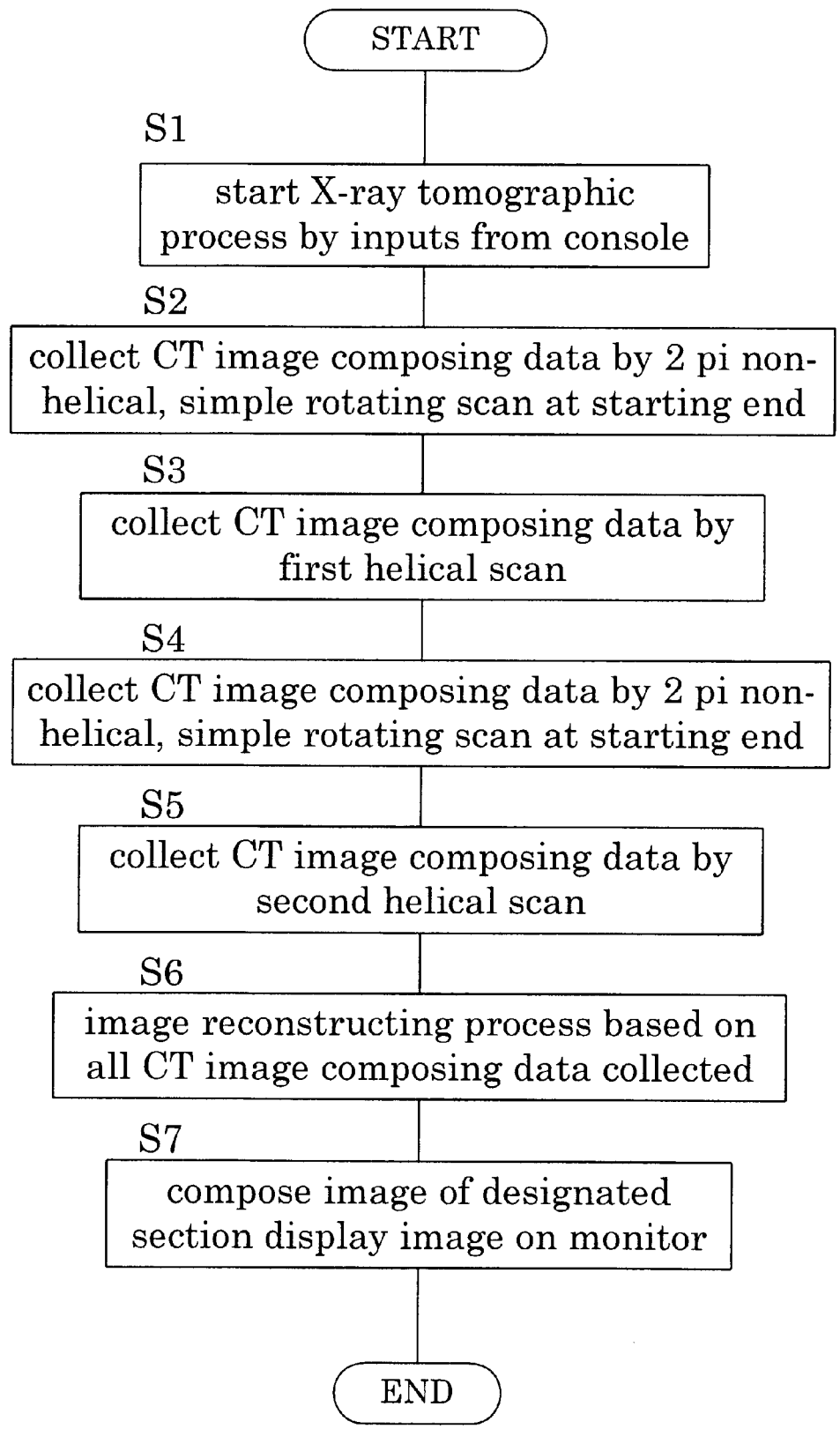
FIG. 12 is a flow chart of a tomographic sequence by the X-ray CT apparatus in the first embodiment.

A process of X-ray tomography by the X-ray CT apparatus in the first embodiment having the above construction will be described next with reference to the drawings. FIG. 12 is a flow chart showing a processing sequence of X-ray tomography by the apparatus in the first embodiment.

The following description will be made starting at a stage where preparations have been made by moving the top board 3 with the patient M placed thereon to set the patient M to a photography starting position.

[Step S1] The operator inputs photographic conditions from the console 12, and starts an X-ray tomographic process.

[Step S2] First, a pre-scan without photography is performed at the starting end of a helical scan. Next, a non-helical, simple rotating scan SC1 of 2π is performed to emit conical X-ray beams CB from the X-ray tube 1 toward the patient M, and collect CT image composing data from the. X-ray detector 2.

[Step S3] The X-ray tube 1 and X-ray detector 2 are driven to advance along the helical path SP1 in the first helical scan to emit conical X-ray beams CB and collect CT image composing data. Upon completion of the first helical scan, the X-ray tube 1 and X-ray detector 2 perform a post-scan, and move to the position for starting the next, second helical scan.

[Step S4] At the terminal end of helical scanning, a pre-scan and non-helical simple rotating scan SC2 of 2π are executed in the opposite direction to those executed at the starting end, to collect CT image composing data similarly.

[Step S5] The X-ray tube 1 and X-ray detector 2 are driven to advance along the helical path SP2 in the second helical scan to collect CT image composing data. Next, a post-scan is executed. In the second helical scan, the scanning direction and rotating direction are reversed from the preceding, first helical scan.

[Step S6] The image reconstructing unit 15 carries out an image reconstructing process based on the CT image composing data for 360° collected through the first and second helical scans and simple rotating scans SC1 and SC2.

[Step S7] Based on results of the reconstructing process, an X-ray CT image of a section designated by the operator is composed and displayed on the screen of a monitor 16.

Since the X-ray CT apparatus in the embodiment described above is the PI-line detection area type, the data collected from the X-ray detector has a relatively simple relationship between respective points in the area of interest and the X-ray detecting elements, and a simplified site-dependent weight function for projection photography as well. Further, CT image composing data for a 360° range is collected by executing helical scans each covering a 180° scanning range, from two directions with an equi-sectional (bisectional) phase difference therebetween. That is, by carrying out an image reconstructing process based on data collected from equal directions, a correction is effected in such a way that artifacts resulting from the non-parallelism of beam elements and the polychroism of X rays cancel each other. Consequently, clear sectional images with the artifacts suppressed are displayed on the monitor 16.

<Second Embodiment>

An X-ray CT apparatus in a second embodiment will be described with reference to the drawings.

Only the aspects of the apparatus in the second embodiment different from those of the apparatus in the preceding, first embodiment will be described. The aspects identical to those of the first embodiment are not described again.

Figure 13:
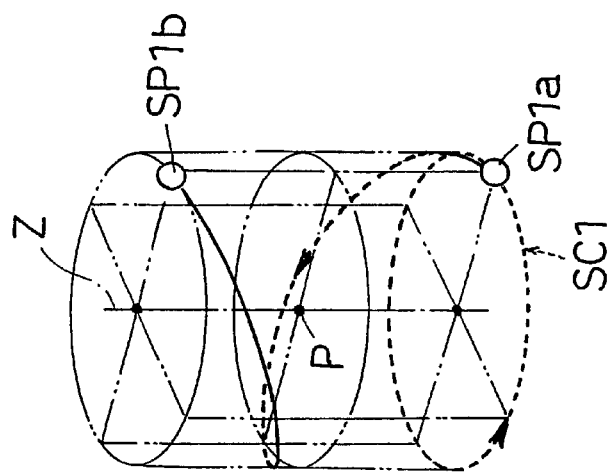
FIG. 13A is an explanatory view of a scan mode by an X-ray CT apparatus in a second embodiment, showing a path of a first helical scan.
FIG. 13B is an explanatory view of a scan mode by the X-ray CT apparatus in the second embodiment, showing a path of a return scan.
FIG. 13C is an explanatory view of a scan mode by the X-ray CT apparatus in the second embodiment, showing a path of a second helical scan.
Figure 13:
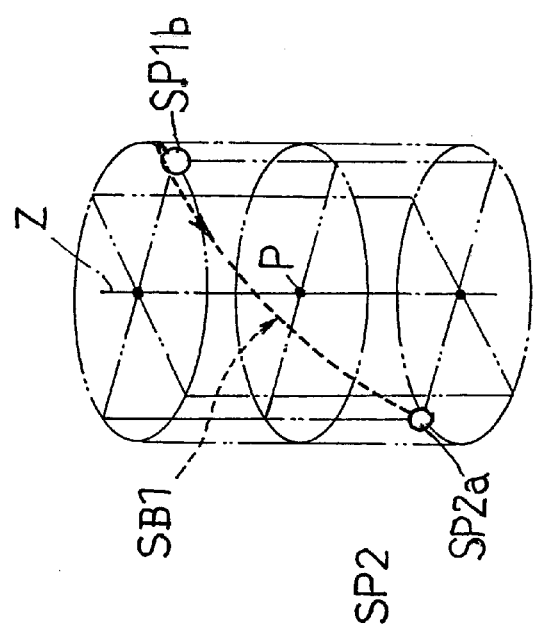
Figure 13:
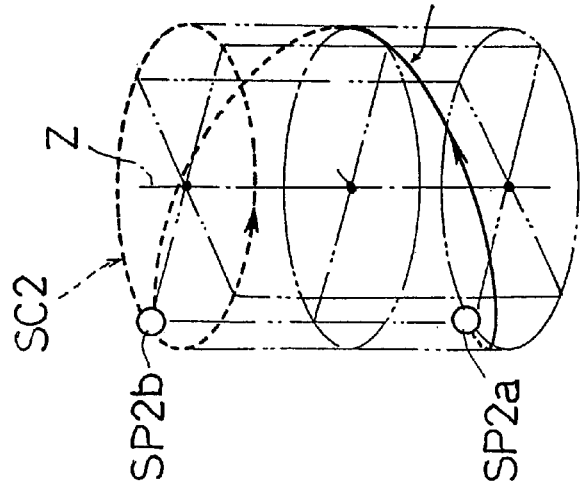
Figure 14:
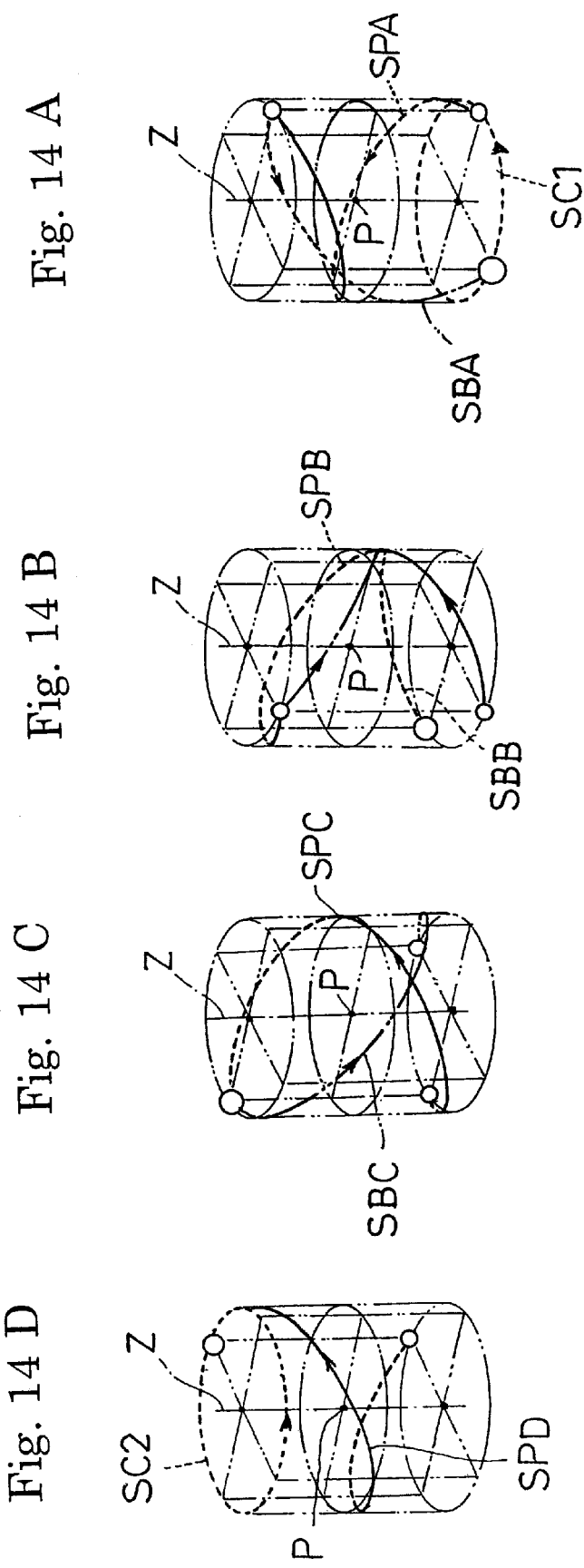
FIG. 14A is an explanatory view of a scan mode by an X-ray CT apparatus in a third embodiment, showing a path of a first helical scan.
FIG. 14B is an explanatory view of a scan mode by the X-ray CT apparatus in the third embodiment, showing paths of a second helical scan and a return scan.
FIG. 14C is an explanatory view of a scan mode by the X-ray CT apparatus in the third embodiment, showing paths of a third helical scan and a return scan.
FIG. 14D is an explanatory view of a scan mode by the X-ray CT apparatus in the third embodiment, showing a path of a fourth helical scan.

In the apparatus in the second embodiment, the X-ray tube 1 and X-ray detector 2 are rotatable constantly in a fixed direction in reciprocally making helical scans from the starting end to the terminal end of an area of interest, and then from the terminal end to the starting end. That is, after executing a first helical scan as shown in FIG. 13A, a return scan SB1 without photography is executed, as shown in FIG. 13B, in the same rotating direction as the preceding, first helical scan, to return the X-ray tube 1 to the end point SP2a at the starting end of the area of interest Ma for executing a second helical scan. Next, as shown in FIG. 13C, the second helical scan is executed in the same scanning direction and rotating direction as the first helical scan.

In the apparatus in the second embodiment, there is no need to switch the scanning direction or rotating direction between the first helical scan and second helical scan. As a result, as in the case of multi-slice CT, the connection between the X-ray tube 1 and high voltage generator may be achieved by slipping technique.

<Third Embodiment>

An X-ray CT apparatus in a third embodiment will be described with reference to the drawings.

Only the aspects of the apparatus in the third embodiment different from those of the apparatus in the preceding, second embodiment will be described. The aspects identical to those of the second embodiment are not described again.

The apparatus in the third embodiment performs four, first to fourth, helical scans successively as shown in FIGS. 14A through 14D. The first to fourth helical scans follow helical paths SPA-SPD shifted by a 90° phase difference (quadrisectional phase difference) from one another. The first to fourth helical scans are intervened by return scans SBA-SBC without photography as shown in chain lines in FIGS. 14A through 14C. The return scans SBA-SBC have the same rotating direction as the first to fourth helical scans, and return the X-ray tube 1 to an end point at the starting end of the area of interest Ma for executing a next helical scan. The X-ray tube 1 returned to the end point performs a helical scan in the same scanning direction and rotating direction as the preceding helical scan.

The X-ray CT apparatus in the third embodiment requires no switching since the first to fourth helical scans have the same scanning direction and rotating direction. Further, by making the four helical scans, CT image composing data may be acquired for the 360° range with twice the density of the data acquired in each of the preceding embodiments. As a result, X-ray CT images ultimately obtained have improved image quality. As in the case of multi-slice CT, the connection between the X-ray tube 1 and high voltage generator may be achieved by slipping technique.

<Fourth Embodiment>

An X-ray CT apparatus in a fourth embodiment will be described with reference to the drawings.

Only the aspects of the apparatus in the fourth embodiment different from those of the apparatus in the preceding, second embodiment will be described. The aspects identical to those of the second embodiment are not described again.

Figure 15:
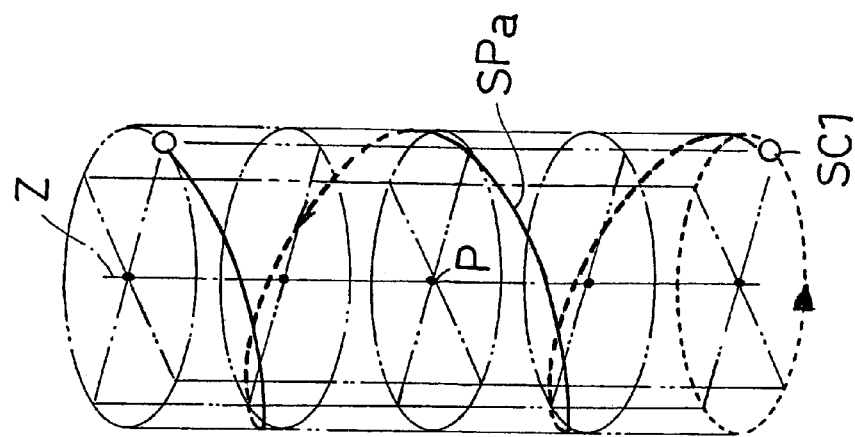
FIG. 15A is an explanatory view of a scan mode by an X-ray CT apparatus in a fourth embodiment, showing a path of a first helical scan.
FIG. 15B is an explanatory view of a scan mode by the X-ray CT apparatus in the fourth embodiment, showing a path of a return scan.
FIG. 15C is an explanatory view of a scan mode by the X-ray CT apparatus in the fourth embodiment, showing a path of a second scan.
Figure 15:
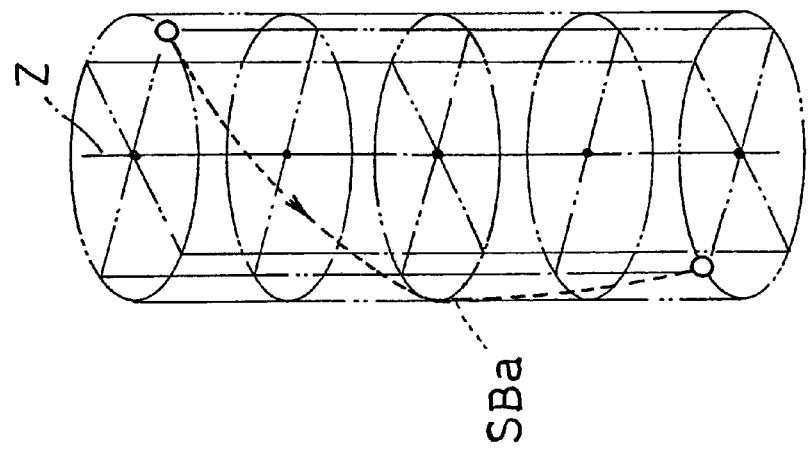
Figure 15:
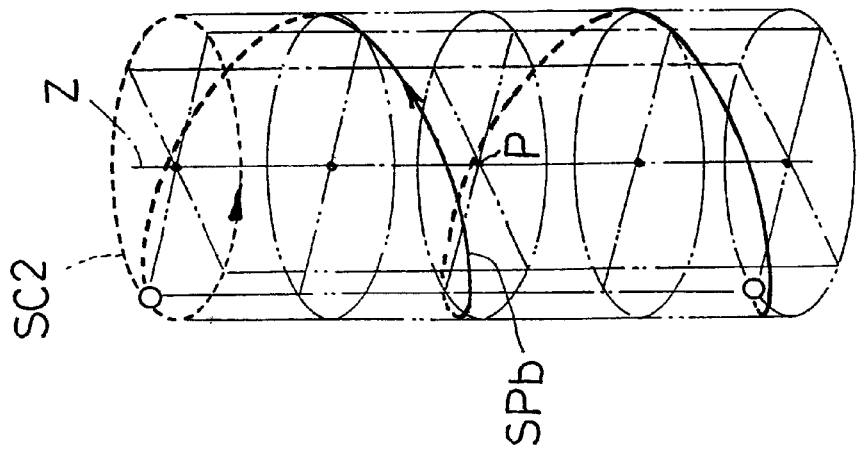

In the apparatus in the fourth embodiment, the X-ray tube 1 makes a first helical scan covering a 4π scanning range by advancing along a helical path SPa circling twice around the patient M as shown by FIG. 15A, and then makes a return scan SBa to return to an end point at the starting end of the area of interest Ma for executing a second helical scan as shown in FIG. 15B. Next, as shown in FIG. 15C, the second helical scan is executed in the same scanning direction and rotating direction as the first helical scan, following a helical path SPb circling twice around the patient M.

Naturally, the helical path SPa for the first helical scan and the helical path SPb for the second helical scan have a 180° phase difference (bisectional phase difference).

In the apparatus in the fourth embodiment also, there is no need to switch the scanning direction or rotating direction between the first helical scan and second helical scan. Further, the range of each helical scan is 4π, twice that of the second embodiment, to be capable of photographing a large area of interest.

Figure 16:
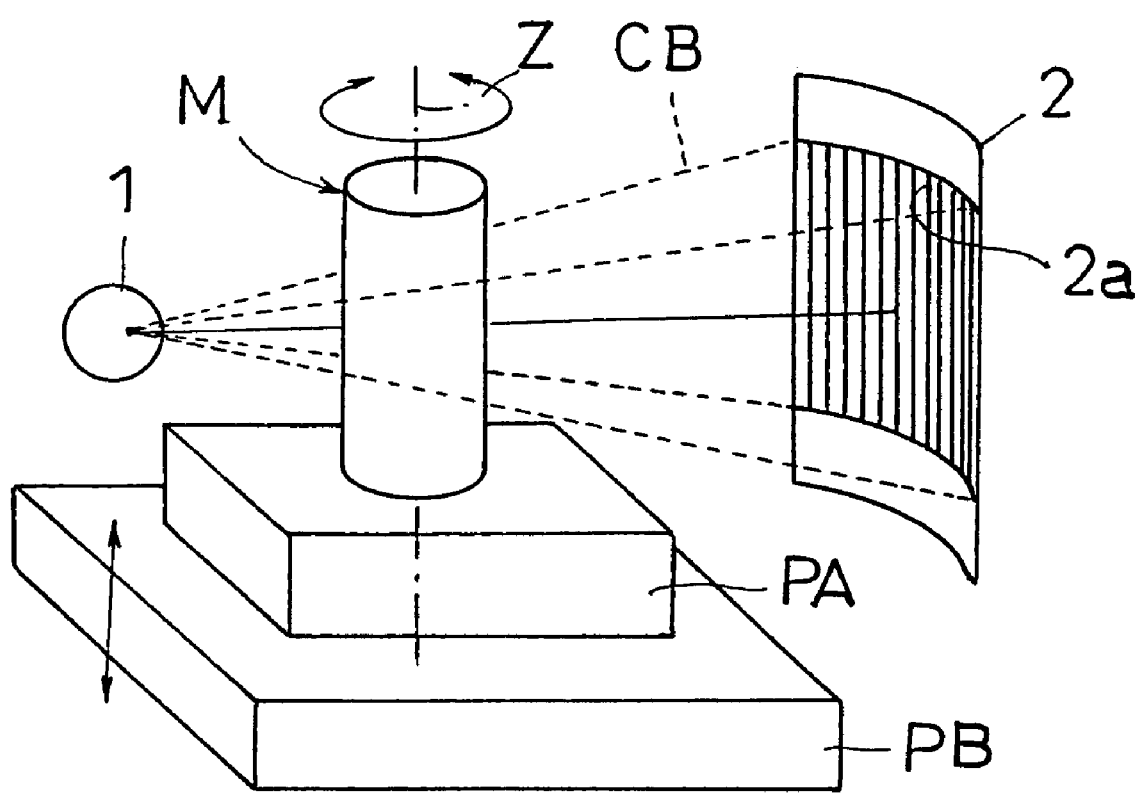
FIG. 16 is a schematic perspective view showing a principal portion a modified apparatus.

This invention is not limited to the foregoing embodiments, but may be modified as follows:

(1) The helical scanning in the apparatus according to this invention may be carried out by rotating an object under examination M and moving the object M along the body axis Z, with the X-ray tube 1 and X-ray detector 2 completely fixed. As shown in FIG. 16, for example, the object M may be placed on a rotatable plate PA which in turn is placed on a lift plate PB that is capable of moving the object M and rotatable plate PA vertically (along the body axis Z of object M). The rotating speed of plate PA and vertically moving speed of lift plate PB may be controlled appropriately by the plural scan controller.

(2) In the foregoing embodiments, the X-ray detector is a panel type X-ray detector. The X-ray detector in the apparatus according to this invention is not limited to a panel type X-ray detector, but may be an image intensifier, for example.

(3) In the foregoing embodiments, an equi-sectional phase difference is set between a plurality of helical scans executed. In the apparatus according to this invention, an equi-sectional phase difference may be set to enable an odd number of helical scans. For example, a 120° may be set to execute three helical scans.

(4) The foregoing embodiments use an X-ray tube that emits X-ray beams in a conical form. It is possible to use, instead of the X-ray tube, a radioactive isotope, a linear accelerator, or an electromagnetic wave source for emitting electromagnetic waves in a range from visible rays to γ-rays. Instead of conical X-ray beams, conical visible light beams or conical γ-ray beams may be used.

(5) In the foregoing embodiments, simple rotating scans of π to 2π are carried out at the opposite ends of each helical scan. Instead, only helical scans may be carried out without the simple rotating scans.

(6) In the foregoing embodiments, a pre-scan is carried out before each effective scan, and a post-scan after each effective scan for stability and protection of the apparatus. Such pre-scan and post-scan may be omitted.

(7) This invention is applicable to a nondestructive testing apparatus for industrial use as well as a diagnostic apparatus for medical use.

The present invention may be embodied in other specific forms without departing from the spirit or essential attributes thereof and, accordingly, reference should be made to the appended claims, rather than to the foregoing specification, as indicating the scope of the invention.

What is claimed is:

1. A CT apparatus for making a plurality of helical scans about an object under examination placed on a support table, and collecting, through each scan, CT image composing data covering a scanning range of 180° for each point in an area of interest, said CT apparatus comprising:

electromagnetic wave emitting means for emitting electromagnetic waves in a conical form toward said object;

planar detecting means opposed to said electromagnetic wave emitting means across said object for detecting the electromagnetic waves emitted from said electromagnetic wave emitting means and diverging two-dimensionally;

drive means for moving said electromagnetic wave emitting means and said planar detecting means relative to said object while rotating said electromagnetic wave emitting means and said planar detecting means about said object, to cause electromagnetic waves to make helical scans around said object, whereby CT image composing data covering a 180° scanning range for each point in the area of interest of said object are collected from said planar detecting means;

plural scan control means for controlling said drive means such that the plurality of helical scans made of said object by said electromagnetic wave emitting means have helical paths with a phase difference therebetween of 360° divided equally; and image reconstructing means for performing an image reconstructing process based on CT image composing data collected through said plurality of helical scans.

2. A CT apparatus as defined in claim 1, wherein said plural scan control means is arranged to control said drive means to execute said helical scans to and fro by alternately reversing a scanning direction and a rotating direction for each scan.

3. A CT apparatus as defined in claim 1, wherein said plural scan control means is arranged to control said drive means to execute said helical scans to and fro and constantly in the same direction of rotation.

4. A CT apparatus as defined in claim 1, wherein said plural scan control means is arranged to control said drive means to execute a non-helical, simple rotating scan in a range of π to 2π at each of opposite ends of each helical scan.

5. A CT apparatus as defined in claim 1, wherein said plural scan control means is arranged to control said drive means to execute said helical scans having a phase difference therebetween of 360° divided equally by an even number.

6. A CT apparatus as defined in claim 1, wherein said plural scan control means is arranged to control said drive means to execute said helical scans having a phase difference therebetween of 360° divided equally by an odd number.

7. A CT apparatus as defined in claim 1, wherein said plural scan control means is arranged to control said drive means to execute said helical scans in a range of π multiplied by a multiple of 2.

8. A CT apparatus as defined in claim 1, wherein said plural scan control means is arranged to control said drive means to execute a pre-scan before starting, and a post-scan after finishing, each helical scan effective to collect CT image composing data, said pre-scan and said post-scan being ineffective to collect CT image composing data.

9. A CT apparatus for making a plurality of helical scans about an object under examination placed on a support table, and collecting, through each scan, CT image composing data covering a scanning range of 180° for each point in an area of interest, said CT apparatus comprising:

electromagnetic wave emitting means for emitting electromagnetic waves in a conical form toward said object;

planar detecting means opposed to said electromagnetic wave emitting means across said object for detecting the electromagnetic waves emitted from said electromagnetic wave emitting means and diverging two-dimensionally;

drive means for moving said electromagnetic wave emitting means and said planar detecting means relative to said object while rotating said support table, to cause electromagnetic waves to make helical scans around said object, whereby CT image composing data covering a 180° scanning range for each point in the area of interest of said object are collected from said planar detecting means;

plural scan control means for controlling said drive means such that the plurality of helical scans made of said object by said electromagnetic wave emitting means have helical paths with a phase difference therebetween of 360° divided equally; and image reconstructing means for performing an image reconstructing process based on CT image composing data collected through said plurality of helical scans.

10. A CT apparatus as defined in claim 9, wherein said plural scan control means is arranged to control said drive means to execute said helical scans to and fro by alternately reversing a scanning direction and a rotating direction for each scan.

11. A CT apparatus as defined in claim 9, wherein said plural scan control means is arranged to control said drive means to execute said helical scans to and fro and constantly in the same direction of rotation.

12. A CT apparatus as defined in claim 9, wherein said plural scan control means is arranged to control said drive means to execute a non-helical, simple rotating scan in a range of $\pi$ to $2\pi$ at each of opposite ends of each helical scan.

13. A CT apparatus as defined in claim 9, wherein said plural scan control means is arranged to control said drive means to execute said helical scans having a phase difference therebetween of 360° divided equally by an even number.

14. A CT apparatus as defined in claim 9, wherein said plural scan control means is arranged to control said drive means to execute said helical scans having a phase difference therebetween of 360° divided equally by an odd number.

15. A CT apparatus as defined in claim 9, wherein said plural scan control means is arranged to control said drive means to execute said helical scans in a range of $\pi$ multiplied by a multiple of 2.

16. A CT apparatus as defined in claim 9, wherein said plural scan control means is arranged to control said drive means to execute a pre-scan before starting, and a post-scan after finishing, each helical scan effective to collect CT image composing data, said pre-scan and said post-scan being ineffective to collect CT image composing data.

* * * * *